United States Patent
Moriya (10) Patent No.: US 8,580,241 B2
(45) Date of Patent: Nov. 12, 2013

(54) GLYCEROL GROUP-CONTAINING ORGANOPOLYSILOXANE, COSMETIC, AND METHOD FOR PRODUCING GLYCEROL GROUP-CONTAINING ORGANOPOLYSILOXANE

(71) Applicant: Shin-Etsu Chemical Co., Ltd., Tokyo (JP)

(72) Inventor: Hiroyuki Moriya, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/632,698

(22) Filed: Oct. 1, 2012

(65) Prior Publication Data

US 2013/0089509 A1  Apr. 11, 2013

(30) Foreign Application Priority Data

Oct. 11, 2011  (JP) ................................. 2011-224092

(51) Int. Cl.
*A61K 31/74* (2006.01)

(52) U.S. Cl.
USPC ..................................................... 424/78.17

(58) Field of Classification Search
None
See application file for complete search history.

(56) References Cited

U.S. PATENT DOCUMENTS

| 4,431,789 A | 2/1984 | Okazaki et al. |
| 2005/0084467 A1 | 4/2005 | Miyanaga |

FOREIGN PATENT DOCUMENTS

| CA | 2219541 A1 | 5/1998 |
| EP | 0 095 676 A2 | 12/1983 |
| EP | 1 359 182 A1 | 11/2003 |
| EP | 1 944 330 A1 | 7/2008 |
| JP | A-57-149290 | 9/1982 |
| JP | A-58-213025 | 12/1983 |
| JP | A-04-020531 | 1/1992 |
| JP | A-09-071504 | 3/1997 |
| JP | A-09-278892 | 10/1997 |
| JP | A-10-158150 | 6/1998 |
| JP | A-10-316526 | 12/1998 |
| JP | A-2004-339244 | 12/2004 |
| WO | WO 2009/150213 A1 | 12/2009 |

OTHER PUBLICATIONS

Jan. 3, 2013 European Search Report issued in Application No. 12006997.6.

*Primary Examiner* — Paul Dickinson
(74) *Attorney, Agent, or Firm* — Oliff & Berridge, PLC

(57) ABSTRACT

There is disclosed a novel glycerol group-containing organopolysiloxane is formed of a glycerol group-containing substituent shown by the following general formula (1) which is bonded to at least one silicon atom of a main chain organopolysiloxane segment,

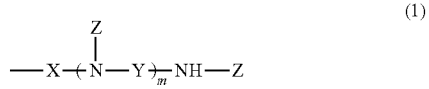

(1)

wherein each X and Y independently represents a divalent hydrocarbon group having 1 to 10 carbon atoms; m represents an integer of 0 to 4; and Z represents an organic group shown by the following general formula (2),

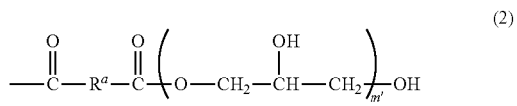

(2)

wherein $R^a$ represents a divalent hydrocarbon group having 2 to 12 carbon atoms; and m' represents an integer of 1 to 5. As a result, there is provided a novel glycerol group-containing organopolysiloxane and a method for producing it without requiring special purification processes, and in addition, provided is a cosmetic not generating an odor with passage of time while giving a moist feeling without stickiness.

13 Claims, 1 Drawing Sheet

GLYCEROL GROUP-CONTAINING ORGANOPOLYSILOXANE, COSMETIC, AND METHOD FOR PRODUCING GLYCEROL GROUP-CONTAINING ORGANOPOLYSILOXANE

BACKGROUND OF THE INVENTION

1. Field of the Invention

The present invention relates to a novel glycerol group-containing organopolysiloxane, a cosmetic containing this, and a method for producing a glycerol group-containing organopolysiloxane.

2. Description of the Related Art

So far, methods for connecting a glycerol group to a silicone (Patent Documents 1 to 4) and compounds obtained by these methods have been disclosed. In these methods, an intended glycerol group-containing organopolysiloxane was obtained by a catalytic addition reaction of a glycerol having a double bond at its terminal ((poly)glycerin having an aliphatic unsaturated bond) or a derivative thereof with a methyl hydrogen polysiloxane.

However, in this method, a starting glycerol having a double bond at its terminal (unreacted glycerol) remains inevitably, so that purification processes such as washing and a hydrogenation reaction are absolutely imperative. It is known that, if these purification processes are not carried out, unpleasant odor is generated with passage of time. Alternatively, a reaction method wherein a hydroxy-containing silicone is reacted with a glycidol in the presence of an acid or a base catalyst is known; but in this method, there is such a problem that breakage or rearrangement of a siloxane chain by presence of an acid or a base catalyst is unavoidable. Further, special purification processes such as neutralization after the reaction and removal of a produced salt are necessary.

A technology to apply a glycerol group-containing organopolysiloxane to a cosmetic has been developed as one application example of this compound (Patent Documents 2, and 4 to 6). However, although a conventional glycerol group-containing organopolysiloxane, if blended in a cosmetic, can give a moist feeling because of its excellent water holding ability, there have been problems of stickiness and poor durability of the moist feeling.

CITATION LIST

Patent Literature

Patent Document 1: Japanese Patent Laid-Open Publication No. H04-20531
Patent Document 2: Japanese Patent Laid-Open Publication No. 2004-339244
Patent Document 3: Japanese Patent Laid-Open Publication No. S57-149290
Patent Document 4: Japanese Patent Laid-Open Publication No. H09-278892
Patent Document 5: Japanese Patent Laid-Open Publication No. H09-71504
Patent Document 6: Japanese Patent Laid-Open Publication No. H10-316526

SUMMARY OF THE INVENTION

The present invention was made in view of the situation as mentioned above and has an object to provide; a novel glycerol group-containing organopolysiloxane and a method for producing it wherein a special purification process to remove an unreacted glycerol—the process having been absolutely imperative—is not necessary; and a cosmetic which does not generate an odor with passage of time while giving a moist feeling without stickiness.

To solve the problems as mentioned above, the present invention provides a glycerol group-containing organopolysiloxane wherein a glycerol group-containing substituent shown by the following general formula (1) is bonded to at least one silicon atom of a main chain organopolysiloxane segment, wherein each X and Y independently represents a divalent hydrocarbon group having 1 to 10 carbon atoms; m represents an integer of 0 to 4; and Z represents an organic group shown by the following general formula (2), wherein $R^a$ represents a divalent hydrocarbon group having 2 to 12 carbon atoms; and m' represents an integer of 1 to 5.

In the novel glycerol group-containing organopolysiloxane like this, purification processes such as washing, a hydrogenation reaction, neutralization, and removal of a neutralized salt, which have been absolutely imperative in the past to obtain a glycerol group-containing organopolysiloxane, are no more necessary; and in addition, a cosmetic containing this compound does not generate an odor with passage of time while giving a moist feeling without stickiness.

Further, it is preferable that the foregoing glycerol group-containing organopolysiloxane be a reaction product between glycidol and an organopolysiloxane having a substituent shown by the following general formula (3) bonded to at least one silicon atom of a main chain organopolysiloxane segment (hereinafter this product may also be referred to as simply "reaction product"), wherein X, Y, and m represent the same meanings as before; and Z' represents an organic group shown by the following general formula (4), wherein $R^a$ represents the same meaning as before.

Accordingly, as to the glycerol group-containing organopolysiloxane, the reaction product as described above may be mentioned.

Meanwhile, although the glycerol group-containing organopolysiloxane of the present invention is the one having an organic group containing a linear glycerol group shown by the general formula (2), there may be a case that the reaction product contains practically an isomer depending on blending composition of glycidol; and thus, in a certain instance, an organopolysiloxane having a branched glycerol group may also be produced as an isomer.

In this case, it is preferable that the glycerol group-containing organopolysiloxane be a compound shown by the following average composition formula (5), wherein each R independently represents a group selected from a hydrogen atom, a hydroxyl group, an alkoxy group having 1 to 3 carbon atoms, an alkyl group having 1 to 30 carbon atoms, a fluoroalkyl group having 1 to 30 carbon atoms, an aryl group having 6 to 30 carbon atoms, and an aralkyl group having 7 to 30 carbon atoms; $R^{10}$ represents a substituent shown by the general formula (1); $R^{11}$ represents a group selected from $R^{10}$ and R; A represents an organopolysiloxane segment shown by the following general formula (6), wherein R and $R^{10}$ represent the same meanings as before, and Q represents an oxygen atom or a divalent hydrocarbon group having 1 to 3 carbon atoms; in the general formulae (5) and (6), each of a, b, and c independently represents an integer of 0 to 3; e represents an integer of 0 to 100; f represents an integer of 0 to 20000; g represents an integer of 0 or 1; h represents an integer of 0 or 1; i represents an integer of 0 to 100; and j represents an integer of 0 to 10000; however, when $R^{11}$ is $R^{10}$, 1≤a+b+c+e+g+i; and when $R^{11}$ is R, 1≤a+b+c+e+i.

As mentioned above, it is preferable that the glycerol group-containing organopolysiloxane be a compound shown by the average composition formula (5).

In addition, the present invention provides a cosmetic wherein the glycerol group-containing organopolysiloxane is contained therein.

The cosmetic of the present invention which contains the glycerol group-containing organopolysiloxane as mentioned above does not generate an odor with passage of time while giving a moist feeling without stickiness.

In addition, the present invention provides a cosmetic wherein the glycerol group-containing organopolysiloxane and a dimethyl polysiloxane having viscosity of 100 $mm^2$/second or less at 25° C. are contained therein.

A cosmetic as mentioned above further suppresses generation of an odor with passage of time while giving a moist feeling with a good spreading property and without sticky and grating feelings.

In addition, the present invention provides a method for producing a glycerol group-containing organopolysiloxane wherein glycidol is reacted with an organopolysiloxane having a substituent shown by the following general formula (3) bonded to at least one silicon atom of a main chain organopolysiloxane segment, wherein each X and Y independently represents a divalent hydrocarbon group having 1 to 10 carbon atoms; m represents an integer of 0 to 4; and Z' represents an organic group shown by the following general formula (4), wherein $R^a$ represents a divalent hydrocarbon group having 2 to 12 carbon atoms.

According to the method of the present invention for producing a glycerol group-containing organopolysiloxane, a novel glycerol group-containing organopolysiloxane having a glycerol group-containing substituent shown by the general formula (1) bonded to at least one silicon atom of a main chain organopolysiloxane segment can be produced.

According to the glycerol group-containing organopolysiloxane of the present invention, a novel glycerol group-containing organopolysiloxane not requiring special purification processes used in the past such as washing, a hydrogenation reaction, neutralization, and removal of a neutralized salt can be obtained; and in addition, a cosmetic containing this novel glycerol group-containing organopolysiloxane does not generate an odor with passage of time while having good durability of a moist feeling without stickiness.

DETAILED DESCRIPTION OF THE PREFERRED EMBODIMENTS

Hereinafter, the present invention will be explained in more detail.

As mentioned above, a novel glycerol group-containing organopolysiloxane and a method for producing it not requiring special purification processes, and in addition, a cosmetic not generating an odor with passage of time while giving a moist feeling without stickiness have been wanted.

Inventors of the present invention carried out an extensive investigation, and as a result, found that a novel glycerol group-containing organopolysiloxane could be obtained by reacting a glycidol with an organopolysiloxane having a carboxyl group bonded by an amide bond. Further, they found that a cosmetic not generating an odor with passage of time while giving a moist feeling without stickiness could be obtained when the novel glycerol group-containing organopolysiloxane obtained by the present invention is blended thereinto.

Hereinafter, the present invention will be explained in more detail.

<Novel Glycerol Group-Containing Organopolysiloxane>

The present invention relates to a novel glycerol group-containing organopolysiloxane wherein a glycerol group-containing substituent shown by the general formula (1) is bonded to at least one silicon atom of a main chain organopolysiloxane segment, wherein each X and Y independently represents a divalent hydrocarbon group having 1 to 10 carbon atoms; m represents an integer of 0 to 4; and Z represents an organic group shown by the following general formula (2), wherein $R^a$ represents a divalent hydrocarbon group having 2 to 12 carbon atoms; and m' represents an integer of 1 to 5.

In the general formula (1), each X and Y independently represents a divalent hydrocarbon group having 1 to 10 carbon atoms; preferably a linear or a branched divalent aliphatic hydrocarbon group having 1 to 10 carbon atoms, or a divalent aromatic hydrocarbon group having 6 to 10 carbon atoms; or more preferably an alkylene or an alkenylene group having 1 to 10 or in particular 2 to 6 carbon atoms, or a phenylene group; among them an ethylene group, an ethylenylene group, a trimethylene group, a propylene group, a butylene group, an isobutylene group, a hexamethylene group, or a phenylene group are preferable. m represents an integer of 0 to 4, or preferably 0 to 2.

In the general formula (2), $R^a$ represents a divalent hydrocarbon group having 2 to 12 carbon atoms; preferably a linear or a branched divalent aliphatic hydrocarbon group having 2 to 12 carbon atoms, or a divalent aromatic hydrocarbon group having 6 to 10 carbon atoms; or more preferably an alkylene or an alkenylene group having 2 to 10 or in particular 2 to 6 carbon atoms, or a phenylene group; among them an ethylene group, an ethylenylene group, a trimethylene group, a propylene group, a butylene group, an isobutylene group, a hexamethylene group, and a phenylene group are still more preferable. m' represents an integer of 1 to 5, preferably 1 to 3, or more preferably 1.

It is preferable that the glycerol group-containing organopolysiloxane of the present invention be a reaction product between glycidol and an organopolysiloxane having a substituent shown by the general formula (3) bonded to at least one silicon atom of a main chain organopolysiloxane segment, wherein X, Y, and m represent the same meanings as before; and Z' represents an organic group shown by the following general formula (4), wherein $R^a$ represents the same meaning as before.

In addition, it is preferable that the glycerol group-containing organopolysiloxane be a compound shown by the following average composition formula (5).

In the general formula (5), each R independently represents a group selected from a hydrogen atom, a hydroxyl group, an alkoxy group having 1 to 3 carbon atoms, an alkyl group having 1 to 30 carbon atoms, a fluoroalkyl group having 1 to 30 carbon atoms, an aryl group having 6 to 30 carbon atoms, and an aralkyl group having 7 to 30 carbon atoms; and specific example thereof includes an alkyl group such as a methyl group, an ethyl group, a propyl group, a butyl group, a pentyl group, a hexyl group, a heptyl group, an octyl group, a nonyl group, a decyl group, a stearyl group, a cyclopentyl group, and a cyclohexyl group; a fluoroalkyl group such as a trifluoropropyl group and a heptadecafluorodecyl group; an aryl group such as a phenyl group and a tolyl group; and an aralkyl group such as a benzyl group and a phenethyl group. Among them, an alkyl group having 1 to 15 carbon atoms and a phenyl group are preferable, though a methyl group is more preferable.

$R^{10}$ represents a substituent shown in the general formula (1); $R^{11}$ represents a group selected from $R^{10}$ and R; and A represents an organopolysiloxane segment shown by the following general formula (6), wherein R and $R^{10}$ represent the same meanings as before; and Q represents an oxygen atom or a divalent hydrocarbon group having 1 to 3 carbon atoms.

In the general formulae (5) and (6), each of a, b, and c independently represents an integer of 0 to 3; e represents an integer of 0 to 100 or preferably 1 to 50; f represents an integer of 0 to 20000 or preferably 20 to 5000; g represents an integer of 0 or 1; h represents an integer of 0 or 1; i represents an integer of 0 to 100 or preferably 1 to 50; and j represents an integer of 0 to 10000 or preferably 20 to 2000; however, when $R^{11}$ is $R^{10}$, $1 \leq a+b+c+e+g+i$; and when $R^{11}$ is R, $1 \leq a+b+c+e+i$.

<Method for Producing the Novel Glycerol Group-Containing Organopolysiloxane>

The glycerol group-containing organopolysiloxane of the present invention uses an organopolysiloxane having a substituent shown by the general formula (3) bonded to at least one silicon atom of a main chain organopolysiloxane segment, which is obtained by reacting an amino-containing organopolysiloxane with a cyclic acid anhydride (organopolysiloxane modified with an amide carboxylic acid). The organopolysiloxane modified with an amide carboxylic acid can be obtained by a method shown in references of public domain, Japanese Patent Laid-Open Publication Nos. S58-213025 and H10-158150. As to the cyclic acid anhydride, one or more compounds selected from phthalic anhydride, succinic anhydride, maleic anhydride, glutaric anhydride, and adipic anhydride may be used.

A solvent used in the reaction between glycidol and the organopolysiloxane modified with an amide carboxylic acid is not limited. The reaction may be carried out without a solvent; but to improve solubility of both compounds, solvents including the following may be used: a hydrocarbon solvent such as hexane and toluene; a ketone solvent such as acetone and methyl ethyl ketone; an amide solvent such as N,N-dimethyl acetamide, N,N-dimethyl formamide, and N-methyl-2-pyrrolidone; an ether solvent such as tetrahydrofuran and 1,4-dioxane; an alcohol solvent such as 2-propanol; an ester solvent such as butyl acetate; and a nitrile solvent such as acetonitrile and benzonitrile. Among them, tetrahydrofuran and acetonitrile are especially preferable. If necessary, a Lewis acid catalyst or a base catalyst may be used; in particular, triethylamine and an alkaline metal hydroxide are preferable. Amount of the catalyst to be added is preferably 0.01 to 1 equivalent, or more preferably 0.02 to 0.1 equivalent, relative to carboxylic acid of the organopolysiloxane modified with an amide carboxylic acid.

Reaction temperature thereof is in the range of 25° C. or higher and not higher than boiling point of glycidol, preferably in the range of 50 to 140° C., or more preferably 60 to 110° C. Reaction time thereof is preferably in the range of 2 to 15 hours, or more preferably 3 to 8 hours.

As to the equivalent amount of the reaction between glycidol and the organopolysiloxane modified with an amide carboxylic acid, equivalent amount of glycidol is preferably 0.1 to 3.0, or more preferably 1.0 to 2.0, relative to carboxylic acid of the organopolysiloxane modified with an amide carboxylic acid.

The glycerol group-containing organopolysiloxane of the present invention may be used, such as for example, in a personal care composition, a cosmetic, a fiber treatment, a coating material, and a polymer property modifier.

<Cosmetic>

Cosmetic of the present invention may contain the glycerol group-containing organopolysiloxane compound of the present invention, especially the glycerol group-containing organopolysiloxane compound produced by the foregoing method, as they are.

Into the cosmetic of the present invention may be added the glycerol group-containing organopolysiloxane of the present invention with the amount thereof being about 0.1 to about 50% by mass relative to totality of the cosmetic, though different in accordance with the kind and formulation thereof.

Into the cosmetic of the present invention may be added, in addition to the glycerol group-containing organopolysiloxane of the present invention, such substances, which are used in a usual cosmetic, as a solid, a semi-solid, or a liquid oil material, water, an alcohol, a water-soluble polymer, a film-forming material, a surfactant, an oil-soluble gelation agent, an organic-modified clay mineral, a resin, powders, a UV-absorber, a moisturizer, preservative, an antibacterial agent, a fragrance, a salt, an antioxidant, a pH controller, a chelating agent, an algefacient, an anti-inflammatory agent, a skin care ingredient, a vitamin, an amino acid, a nucleic acid, a hormone, and a clathrate compound. Hereinafter, illustrative example thereof will be mentioned, though the present invention is not restricted by them.

As to the oil material usable in the present invention, following substances may be mentioned. Meanwhile, POE means polyoxyethylene. Illustrative example of the natural vegetable and animal fatty oil and the semi-synthetic oil includes an avocado oil, a linseed oil, an almond oil, an insects wax, a perilla oil, an olive oil, a cocoa butter, a kapok wax, a kaya oil, a carnauba wax, a liver oil, a candelilla wax, a beef tallow, a neats-foot oil, a beef bone fat, a cured beef tallow, an apricot kernel oil, a whale wax, a hydrogenated oil, a wheat germ oil, a sesame oil, a rice germ oil, a rice bran oil, a sugarcane wax, a sasanqua oil, a safflower oil, a shea butter, a Chinese tung oil, a cinnamon oil, a jojoba wax, a shellac wax, a turtle oil, a soybean oil, a tea seed oil, a camellia oil, an evening primrose oil, a corn oil, a pig fat, a rapeseed oil, a Japanese tung oil, a bran wax, a germ oil, a horse fat, a persic oil, a palm oil, a palm kernel oil, a castor oil, a cured castor oil, a methyl ester of cured castor oil fatty acid, a sunflower oil, a grape seed oil, a bayberry wax, a jojoba oil, a macademia nut oil, a bees wax, a mink oil, a cotton seed oil, a cotton wax, a Japan wax, a Japan wax kernel oil, a montan wax, a coconut oil, a cured coconut oil, a tri-coconut fatty acid glyceride, a mutton tallow, a peanut oil, lanolin, liquid lanolin, reduced lanolin, lanolin alcohol, hard lanolin, lanolin acetate, isopropyl lanolin fatty acid, POE lanolin alcohol ether, POE lanolin alcohol acetate, polyethylene glycol lanolin fatty acid, POE hydrogenated lanolin alcohol ether, and an egg-yolk oil.

Illustrative example of the hydrocarbon oil includes an ozocerite, squalane, squalene, a ceresin, a paraffin, a paraffin wax, a liquid paraffin, a pristane, polyisobutylene, a microcrystalline wax, and vaseline. Illustrative example of the higher fatty acid includes lauric acid, myristic acid, palmitic acid, stearic acid, behenic acid, undecylenic acid, oleic acid, linoleic acid, linolenic acid, arachidonic acid, eicosapentaenoic acid, docosahexaenoic acid, isostearic acid, and 12-hydroxystearic acid.

Illustrative example of the higher alcohol includes lauryl alcohol, myristyl alcohol, palmityl alcohol, stearyl alcohol, behenyl alcohol, hexadecyl alcohol, oleyl alcohol, isostearyl alcohol, hexyl dodecanol, octyl dodecanol, cetostearyl alcohol, 2-decyl tetradecynol, cholesterol, phytosterol, POE cholesterol ether, monostearyl glycerin ether (batyl alcohol), and monooleyl glycerin ether (selachyl alcohol).

Illustrative example of the ester oil includes diisobutyl adipate, 2-hexyldecyl adipate, di-2-heptylundecyl adipate, an N-alkylglycol monoisostearate, isocetyl isostearate, trimethylolpropane triisostearate, ethylene glycol di-2-ethylhexanoate, neopentyl glycol di-2-ethylhexanoate, cetyl 2-ethylhexanoate, trimethylolpropane tri-2-ethylhexanoate, pentaerythritol tetra-2-ethylhexanoate, cetyl octanoate, octyl dodecyl gum ester, oleyl oleate, octyldodecyl oleate, decyl oleate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, a dipentaerythritol fatty acid ester, isopropyl myristate, 2-octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate ester, diisostearyl malate, dextrin palmitate ester, dextrin stearate ester, dextrin 2-ethylhexanoate palmitate ester, sucrose palmitate ester, sucrose stearate ester, monobenzylidene sorbitol, and dibenzylidene sorbitol.

Illustrative example of the glyceride oil includes acetoglyceryl, glyceryl diisooctanoate, glyceryl triisostearate, glyceryl triisopalmitate, glyceryl tri-2-ethylhexanoate, glyceryl monostearate, glyceryl di-2-heptylundecanoate, and glyceryl trimyristate.

Illustrative example of the silicone oil includes dimethyl polysiloxane, methyl phenyl polysiloxane, methyl hydrogen polysiloxane, octamethyl cyclotetrasiloxane, decamethyl cyclopentasiloxane, dodecamethyl cyclohexasiloxane, tetramethyl tetrahydrogen cyclotetrasiloxane, a silicone modified with a higher alkoxy such as stearoxysilicone, a higher fatty acid-modified silicone, a fluorine-modified silicone, an amino-modified silicone, an alkyl-modified silicone, a silicone modified with a higher aliphatic acid ester, a silicone resin, a silicone rubber, and a silicone resin. Illustrative example of the fluorinated oil material includes perfluoro polyether, perfluoro decalin, and perfluoro octane. Especially concurrent use of a dimethyl polysiloxane having viscosity of 100 mm$^2$/second or less at 25° C. can bring a moist feeling and a good spreading property without a grating feeling; and thus, this can be suitably used in the cosmetic of the present invention.

These oil materials may be used singly, or as a mixture of two or more of them, as appropriate. The cosmetic of the present invention may contain the oil material with the amount thereof being 0 to 90.0% by mass, especially preferably 1 to 90% by mass. If the cosmetic of the present invention contains water as its ingredient, amount of water therein is 0 to 99.0% by mass.

Illustrative example of the alcohol usable in the present invention includes ethanol, propanol, ethylene glycol, ethylene glycol monoalkyl ether, diethylene glycol monoethyl ether, polyethylene glycol, propylene glycol, dipropylene glycol, 1,3-butylene glycol, glycerin, diglycerin, polyglycerin, pentaerythritol, sucrose, lactose, xylitol, sorbitol, mannitol, maltitol, carrageenan, agar, guar gum, dextrin, tragacanth gum, locust bean gum, polyvinyl alcohol, polyoxyethylene polymer, polyoxyethylene polyoxypropylene copolymer, hyaluronic acid, chondroitin sulfate, and chitin chitosan; these may be used singly or as a mixture of two or more of them as appropriate. Amount of these alcohols in the cosmetic is in the range of 0.1 to 90.0% by mass, or preferably 0.5 to 50.0% by mass. If the amount thereof is 0.1% or more, sufficient moist property, antibacterial property, and antifungal property may be obtained; while, if the amount thereof is 90.0% by mass or less, effect of powder composition of the present invention may be fully expressed; and thus this range is desirable.

The cosmetic of the present invention is excellent with only those ingredients mentioned above, but can further contain following (i), (ii), (iii), and (iv), if necessary.

(i) Any one of following powder and colorant or both Illustrative example of the inorganic powder includes a powder of titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, golden mica, pink mica, black mica, lithia mica, silicic acid, anhydrous silicic acid, aluminum silicate, magnesium silicate, aluminum magnesium silicate, calcium silicate, barium silicate, strontium silicate, a metal tungstate salt, hydroxy apatite, vermiculite, higilite, bentonite, montmorillonite, hectorite, zeolite, ceramic powder, dicalcium phosphate, alumina, aluminum hydroxide, boron nitride, and silica.

Illustrative example of the organic powder includes polyamide powder, polyester powder, polyethylene powder, polypropylene powder, polystyrene powder, polyurethane powder, benzoguanamine powder, polymethyl benzoguanamine powder, tetrafluoroethylene powder, polymethyl methacrylate powder, cellulose powder, silk powder, nylon powder such as 12 nylon and 6 nylon, and other powders of styrene-acrylic acid copolymer, divinyl benzene-styrene copolymer, a vinyl resin, an urea resin, a phenolic resin, a fluorinated resin, a silicone resin, an acryl resin, a melamine resin, an epoxy resin, a polycarbonate resin, fine crystalline fiber powder, a starch, and lauroyl lysine.

Illustrative example of the surfactant metal salt powder (metal soap) includes zinc stearate, aluminum stearate, calcium stearate, magnesium stearate, zinc myristate, magnesium myristate, zinc cetylphosphate, calcium cetylphosphate, and sodium cetylphosphate zinc.

Illustrative example of the color pigment includes an inorganic red pigment such as iron oxide, iron hydroxide, and iron titanate; an inorganic brown pigment such as γ-iron oxide; an inorganic yellow pigment such as yellow iron oxide and yellow earth; an inorganic black pigment such as black iron oxide and carbon black; an inorganic purple pigment such as manganese violet and cobalt violet; an inorganic green pigment such as chromium hydroxide, chromium oxide, cobalt oxide, and cobalt titanate; an inorganic blue pigment such as Prussian blue and azurite; a laked tar dye; a laked natural dye; and a composite powder obtained by hybridization of these powders.

Illustrative example of the pearl pigment includes a mica coated with titanium oxide, oxychloro bismuth, oxychloro bismuth coated with titanium oxide, talc coated with titanium oxide, fish scale foil, and color mica coated with titanium oxide; and illustrative example of the metal powder pigment includes aluminum powder, copper powder, and stainless powder.

Illustrative example of the tar dye includes Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207; and illustrative example of the natural dye includes carminic acid, laccaic acid, carthamin, brazilin, and crocin.

These powders may be used independent of their forms (spherical, needle-like, plate-like, and so on), their particle diameters (fumed, microparticle, pigment-class, and so on), and their particle structures (porous, non-porous, and so on), as far as they are used in a usual cosmetic. Further, these powders may form a composite by hybridizing them, or may be treated their surfaces with a silicone or a fluorinated compound other than the glycerol group-containing organopolysiloxane compound of the present invention.

(ii) Surfactants Shown Below

Illustrative example of the anionic surfactant includes, a saturated or an unsaturated aliphatic acid soap such as sodium stearate and triethanolammonium oleate, an alkyl ether carboxylic acid and a slat thereof, a carboxylate salt of a condensation product between an amino acid and a fatty acid or the like, an amide ether carboxylate salt, an α-sulfofatty acid ester salt, an α-acylsulfonate salt, an alkyl sulfonate salt, an alkene sulfonate salt, a sulfonate salt of a fatty acid ester, a sulfonate salt of a fatty acid amide, an alkyl sulfonate salt and a sulfonate salt of its formalin condensate, an alkyl sulfate ester salt, a sulfate ester salt of a secondary higher alcohol, a sulfate ester salt of an alkyl and an allyl ether, a sulfate ester salt of a fatty acid ester, a sulfate ester salt of a fatty acid alkylolamide, a sulfate ester salt of a Turkey red oil and so on, an alkyl phosphate salt, an alkenyl phosphate salt, an ether phosphate salt, an alkyl ally ether phosphate salt, an alkylamide phosphate salt, and an N-acylamino acid.

Illustrative example of the cationic surfactant includes an alkylamine salt, a salt of an amine such as polyamine and an aminoalcohol fatty acid derivative, an alkyl quaternary ammonium salt, an aromatic quaternary ammonium salt, a pyridinum salt, and an imidazolium salt.

Illustrative example of the nonionic surfactant includes a sorbitan fatty acid ester, a glycerin fatty acid ester, a polyglycerin fatty acid ester, a propylene glycol fatty acid ester, a polyethylene glycol fatty acid ester, a sucrose fatty acid ester, a polyoxyethylene alkyl ether, a polyoxypropylene alkyl ether, a polyoxyethylene alkyl phenyl ether, a polyoxyethylene fatty acid ester, a polyoxyethylene sorbitan fatty acid ester, a polyoxyethylene sorbitol fatty acid ester, a polyoxyethylene glycerin fatty acid ester, a polyoxyethylene propylene glycol fatty acid ester, a polyoxyethylene castor oil, a polyoxyethylene hard castor oil, a polyoxyethylene phytostanol ether, a polyoxyethylene phytosterol ether, a polyoxyethylene cholestanol ether, a polyoxyethylene cholesteryl ether, a polyoxyalkylene-modified organopolysiloxane, an organopolysiloxane co-modified with a polyoxyalkylene and an alkyl, an organopolysiloxane co-modified with a polyoxyalkylene and a fluoroalkyl, a polyoxyalkylene-organopolysiloxane block copolymer, an alkanol amide, a sugar ether, and a sugar amide.

Illustrative example of the amphoteric surfactant includes a betaine, an aminocarboxylic acid salt, and an imidazoline derivative.

(iii) Crosslinking Organopolysiloxane

The cosmetic of the present invention may contain one, or two or more of crosslinking organopolysiloxanes according to its purpose. It is preferable that this crosslinking organopolysiloxane swell by absorbing the low viscous silicone having viscosity of 0.65 to 10.0 mm$^2$/second (25° C.) with the amount thereof being more than own weight of the crosslinking organopolysiloxane. In addition, it is preferable that this crosslinking organopolysiloxane have a crosslinking structure formed by reaction between a crosslinking agent having two or more reactive vinyl groups in its molecule and a hydrogen atom directly bonded to a silicon atom. Further, it is preferable that this crosslinking organopolysiloxane have at least one moiety selected from the group consisting of a polyoxyalkylene moiety, an alkyl moiety, an alkenyl moiety, an aryl moiety, and a fluoroalkyl moiety. If this crosslinking organopolysiloxane is used, amount thereof is preferably in the range of 0.1 to 30% by mass, in particular 1 to 10% by mass, relative to totality of the cosmetic.

(iv) Silicone Resin Such as a Graft or a Block Acryl/Silicone Copolymer and a Silicone Network Compound In the cosmetic of the present invention, at least one silicone resin selected from a graft or a block acryl/silicone copolymer, a silicone network compound, and the like may be used. In the present invention, an acryl silicone resin is especially preferable as this silicone resin. Further, it is preferable that this silicone resin be an acryl silicone resin containing in its molecule at least one moiety selected from the group consisting of a pyrrolidone moiety, a long-chain alkyl moiety, a polyoxyalkylene moiety, and a fluoroalkyl moiety. In addition, it is preferable that this silicone resin be a silicone network compound. When a silicone resin such as the graft or block acryl/silicone copolymer and the silicone network compound is used, amount thereof to be blended is preferably 0.1 to 20% by mass, in particular 1 to 10% by mass, relative to totality of the cosmetic.

Specific application of the cosmetic of the present invention includes a make-up product, a hair cosmetic, and a UV-cut product. Form of the product thereof is not particularly restricted; and it may be used as such states as a liquid, a emulsion, a cream, a solid, a paste, a gel, a powder, a multi-layer, a mousse, and a spray.

As the most preferable application of the cosmetic of the present invention, a hair cosmetic may be mentioned. Amount of the organopolysiloxane compound of the present invention in the hair cosmetic is 0.1 to 20% by mass (hereinafter, merely shown by %), more preferably 1 to 10%, or still more preferably 1 to 5% in order to have good conditioning effect and its durability.

The hair cosmetic of the present invention may be further blended with an oil material, especially an oil material having a conditioning effect to hairs. Illustrative example of the oil material includes a lower alcohol, a saturated or an unsaturated alcohol having 12 to 30 carbon atoms; an ether of the foregoing alcohol with a polyalcohol; an ester of the foregoing alcohol with an aliphatic acid having 1 to 11 carbon atoms; a saturated or an unsaturated aliphatic acid having 12 to 30 carbon atoms; an ester of the foregoing aliphatic acid with a monovalent or a polyvalent alcohol; an amide of the foregoing aliphatic acid with an amine; a sterol; squalane; a phosphorous lipid; a sugar lipid; an animal fat; a vegetable fat; and one or more silicones selected from a cyclic, a linear, or a branched dimethyl polysiloxane, methyl polysiloxane, polysiloxane, alkyl-modified silicone, methyl phenyl polysiloxane, and polyether-modified silicone.

Amount of these oil materials blended into the hair cosmetic is preferably 0.01 to 30%, more preferably 1 to 25%, or still more preferably 3 to 20%.

In addition, the hair cosmetic of the present invention may be added as appropriate with a thickener such as hydroxyethyl cellulose, a surfactant, an anionic, an amphoteric, a cationic, or a nonionic polymer, a fragrance, a material to afford a pearl-like appearance, a hair-setting polymer, a color pigment, an UV absorber, an antioxidant, and a preservative.

There is no particular restriction as to the surfactant provided that it is used in a usual hair cosmetic; and thus, any of an anionic, a nonionic, an amphoteric, and a cationic surfactant may be used suitably.

Specific example of the anionic surfactant includes an alkylbenzene sulfonate salt, preferably a linear or a branched alkylbenzene sulfonate salt having an alkyl group having average 10 to 16 carbon atoms; an alkyl ether sulfate salt or an alkenyl ether sulfate salt, preferably an alkyl ether sulfate salt or an alkenyl ether sulfate salt having a linear or a branched alkyl or alkenyl group having average 10 to 20 carbon atoms, wherein the alkyl ether sulfate salt or the alkenyl ether sulfate salt is an adduct of ethylene oxide, propylene oxide, or butylene oxide with the average number thereof in one molecule being 0.5 to 8 mole and with molar ratio of ethylene oxide to propylene oxide being 0.1/9.9 to 9.9/0.1 or ethylene oxide to butylene oxide being 0.1/9.9 to 9.9/0.1; an alkylsulfate salt or an alkenylsulfate salt, preferably an alkylsulfate salt or an alkenylsulfate salt having an alkyl group or an alkenyl group having average 10 to 20 carbon atoms; an olefin sulfonate salt, preferably an olefin sulfonate salt having average 10 to 20 carbon atoms in one molecule; an alkane sulfonate salt, preferably an alkane sulfonate salt having average 10 to 20 carbon atoms in one molecule; a higher fatty acid salt, preferably a saturated or an unsaturated fatty acid salt having average 10 to 24 carbon atoms in one molecule; a surfactant of an (amide) ether carboxylic acid type; an α-sulfo fatty acid salt or ester thereof, preferably an α-sulfo fatty acid salt or ester thereof having an alkyl group or an alkenyl group having average 10 to 20 carbon atoms; a surfactant of an N-acyl aminoacid type, preferably a surfactant of an N-acyl aminoacid type having a free carboxylic acid residue and an acyl group having 8 to 24 carbon atoms (for example, N-acyl sarcosinate and N-acyl-β-alanine); a surfactant of a phosphate ester type, preferably a surfactant of a phosphate mono- or di-ester type having an alkyl group, an alkenyl group, or an alkylene oxide adduct thereof having 8 to 24 carbon atoms; a surfactant of a sulfosuccinate ester type, preferably a surfactant of a sulfosuccinate ester of a higher alcohol having 8 to 22 carbon atoms or an ethoxylate thereof or a sulfosuccinate ester derived from a higher aliphatic acid amide; a polyoxyalkylene fatty acid amide ether sulfate salt, preferably a sulfate salt of an ethoxylate and so forth of a linear or a branched, a saturated or an unsaturated, aliphatic acid monoethanol amide or diethanol amid having 8 to 24 carbon atoms; a monoglyceride sulfate ester salt, preferably a monoglyceride sulfate ester salt having a linear or a branched, a saturated or an unsaturated, aliphatic acid group having 8 to 24 carbon atoms; an acylated isethionate salt, preferably an acylated isethionate salt having a linear or a branched, a saturated or an unsaturated, aliphatic acid group having 8 to 24 carbon atoms; an alkyl glyceryl ether sulfate salt or an alkyl glyceryl ether sulfonate salt, preferably an alkyl glyceryl ether sulfate salt or an alkyl glyceryl ether sulfonate salt having a linear or a branched alkyl group, alkenyl group, or alkylene oxide adduct of them having 8 to 24 carbon atoms; an alkyl or an alkenyl amide sulfonate, preferably an alkyl or an alkenyl amide sulfonate having a linear or a branched alkyl or alkenyl group having 8 to 24 carbon atoms; an alkanol amide sulfosuccinate salt, preferably an alkanol amide sulfosuccinate salt having a linear or a branched alkyl or alkenyl group having 8 to 24 carbon atoms; an alkyl sulfoacetate, preferably an alkyl sulfoacetate having a linear or a branched alkyl or alkenyl group having 8 to 24 carbon atoms; an acylated taurate, preferably an acylated taurate having a linear or a branched, a saturated or an unsaturated, aliphatic acid group having 8 to 24 carbon atoms; an N-acyl-N-carboxyethyl glycine salt, preferably an N-acyl-N-carboxyethyl glycine salt having an acyl group having 6 to 24 carbon atoms.

Illustrative example of the counter ion of these anionic surfactant salt, namely the counter ion of an anionic residue thereof includes an alkaline metal ion such as sodium and potassium; an alkaline earth metal ion such as calcium and magnesium; and an alkanol amine having 1 to 3 alkanol group having 2 or 3 carbon atoms (for example, monoethanol amine, diethanol amine, triethanol amine, and triisopropanol amine).

Among these anionic surfactants, an alkyl ether sulfate salt, in particular, a polyoxyethylene alkyl ether sulfate salt is preferable.

Illustrative example of the nonionic surfactant includes a polyoxyalkylene alkyl ether or a polyoxyalkylene alkenyl ether having a linear or a branched alkyl or alkenyl group having average 10 to 24 carbon atoms and having an adduct of ethylene oxide, propylene oxide, or butylene oxide; a glycerin ester of a fatty acid having 8 to 20 carbon atoms; a glycol ester of a fatty acid having 8 to 20 carbon atoms; an alkylene oxide adduct of monoglyceride of a fatty acid having 8 to 20 carbon atoms; a sucrose ester of a fatty acid having 8 to 20 carbon atoms; a sorbitan ester of a fatty acid having 8 to 20 carbon atoms; a polyglycerin fatty acid ester having an acyl group having 8 to 20 carbon atoms; a monoethanol amide, diethanol amide, or their ethoxylate of a fatty acid having 8 to 20 carbon atoms; a polyoxyethylene hard castor oil; a polyoxyethylene sorbitol fatty acid ester having an acyl group having 8 to 20 carbon atoms; a polyoxyethylene sorbit fatty acid ester having an acyl group having 8 to 20 carbon atoms; an alkyl saccharide surfactant having a linear or a branched alkyl group having 8 to 18 carbon atoms, an alkenyl group, or an alkyl phenyl group; an alkylamine oxide or an alkylamide amine oxide having a linear or a branched alkyl group having 8 to 20 carbon atoms, or an alkenyl group; an ether compound or an ester compound of a polyalcohol having a linear or a branched alkyl group having 8 to 20 carbon atoms, or an alkenyl group; an organopolysiloxane modified with polyoxyalkylene; an organopolysiloxane co-modified with polyoxyalkylene and an alkyl; an organopolysiloxane modified with polyglycerin; an organopolysiloxane co-modified with polyglycerin and an alkyl; an organopolysiloxane co-modified with a polyoxyalkylene and a fluoroalkyl; a crosslinking polyoxyalkylene organopolysiloxane; a sugar-modified silicone; an oxazoline-modified silicone; a polyoxyalkylene alkyl aryl ether; a polyoxyalkylene lanolin alcohol; a polyoxyalkylene fatty acid ester; a pluronic block polymer; a tetronic block polymer; a polyoxyalkylene fatty acid amide; a polyoxyalkylene alkylamide; and a polyethylene imine derivative.

As to the amphoteric surfactant, there is no particular restriction provided that it is used in a usual hair cosmetic; and illustrative example thereof includes an amide amine type, a carbobetaine type, an amide betaine type, a sulfobetaine type, an amide sulfobetaine type, an imidazolinium betaine type, an aminoacid type, a phosphobetaine type, and a phosphate ester type.

As to the cationic surfactant, a tertiary amine, a quaternary ammonium salt, an amide amine, an ester amine, and so forth may be mentioned. Illustrative example thereof includes behenyl trimethyl ammonium chloride, distearyl dimethyl ammonium chloride, cetyl trimethyl ammonium chloride, stearyl trimethyl ammonium chloride, lauryl trimethyl ammonium chloride, N-stearyl-N,N,N-tri(polyoxyethylene) ammonium chloride (addition of total 3 ethylene oxides), cetyl benzyl dimethyl ammonium chloride, cetyl triethyl ammonium chloride, distearyl dimethyl ammonium chloride, 2-decyltetradecyl trimethyl ammonium chloride, 2-dodecylhexadecyl trimethyl ammonium chloride, di-2-hexyldecyl dimethyl ammonium chloride, di-2-octyldodecyl dimethyl ammonium chloride, behenyl tertiary amine, stearyl tertiary amine, and stearamidepropyl dimethyl amine.

These surfactants may be used singly or as a mixture of two or more of them; and in order to have a good foaming property, amount thereof in the hair cosmetic is preferably 0.1 to 50%, more preferably 0.5 to 40%, and in particular 1 to 30%.

When the hair cosmetic of the present invention is in a form of hair setting, hair foaming, hair spray, and so forth, it is preferable to contain following exemplified polymers as a hair setting polymer therein:
polyvinyl pyrrolidone; copolymer of polyvinyl pyrrolidone and vinyl acetate; crosslinked copolymer of polyvinyl pyrrolidone, vinyl acetate, and vinyl propionate; copolymer of polyvinyl pyrrolidone and an alkyl aminoacrylate; copolymer of polyvinyl pyrrolidone, an acrylate, and (meth)acrylic acid; copolymer of polyvinyl pyrrolidone, an alkyl aminoacrylate, and vinyl caprolactam;
copolymer of methyl vinyl ether and a maleic anhydride alkyl half ester;
copolymer of vinyl acetate and crotonic acid; copolymer of vinyl acetate, crotonic acid, and vinyl neodecanoic acid, copolymer of vinyl acetate, crotonic acid, and vinyl propionate, copolymer of vinyl acetate, vinyl tert-butylbenzoic acid, and crotonic acid;
copolymer of (meth)acrylic acid and a (meth)acrylate ester, copolymer of acrylic acid, an alkly acrylate ester, and an alkyl acrylamide;
copolymer of (meth)acryl ethyl betaine and an alkyl(meth) acrylate ester; copolymer of N-methacryloyloxyethyl-N,N-dimethyl ammonium α-N-methylcarboxy betaine and an alkyl(meth)acrylate ester; copolymer of an alkyl acrylate ester, butylaminoethyl methacrylate, and acrylic acid octylamide;
a basic acryl polymer;
a compound having a cellulose skeleton and a cationic cellulose derivative;
a salt of hydroxypropyl chitosan, carboxymethyl chitin, carboxymethyl chitosan, and chitosan with a monovalent acid such as pyrrolidone carboxylic acid, lactic acid, and glycol acid or with a divalent acid such as adipic acid and succinic acid; and
a water-dispersible polyester.

These hair setting polymers may be used singly or as a mixture of two or more of them. Amount of the hair setting polymer in the cosmetic is preferably 0.1 to 10%, more preferably 0.5 to 6%, or in particular 1 to 4%, to obtain a sufficient and necessary setting power.

Illustrative example of the hair cosmetic includes materials used in a home place and a beauty salon; and thus, those used in a bath room, such as a hair shampoo, a hair treatment, and a hair conditioner; those used outside a bath room, such as a hair foam, a hair spray, a hair cream, a hair wax, and a hair gel; and in addition, a hair dye, a hair permanent, a hair manicure, and a hair bleach. The organopolysiloxane compound of the present invention may be blended to any of them.

EXAMPLES

Hereinafter, the present invention will be explained concretely by showing Preparation Examples, Comparative Preparation Examples, Examples, and Comparative Examples; but the present invention is not limited to the following Examples. Meanwhile, amounts of respective ingredients not having a special note in the Table are based on amount of a pure substance thereof.

Preparation Example 1

Into a reactor were taken 300 parts by mass of an amino-modified organopolysiloxane shown by the following average composition formula with viscosity of 38 mm$^2$/second (25° C.) and amine equivalent of 2500 g/mol, 50 parts by mass of tetrahydrofuran, and 12 parts by mass of succinic anhydride; and then, the resulting mixture was stirred at 50° C. for 3 hours. The reaction mixture thus obtained was stripped to remove the solvent under reduced pressure at 110° C. to obtain a colorless, transparent liquid having viscosity of 550 mm$^2$/second (25° C.). The carboxy equivalent of this liquid was 2630 g/mol, so that it was confirmed that conversion to the amidecarboxylic acid took place.

Then, 150 parts by mass of the liquid thus obtained and 6 parts by mass of glycidol were stirred in a different reactor at 110° C. for 8 hours. The reaction mixture thus obtained was stripped to remove the unreacted substance under reduced pressure at 120° C. to obtain a pale yellow, transparent liquid having viscosity of 4400 mm$^2$/second (25° C.). Meanwhile, special purification processes such as washing, a hydrogenation reaction, neutralization, and removal of a neutralized salt were not carried out. From the measurement result (FIG. 1) of 1H NMR (CDC13, 400 MHz, manufactured by Bruker Corp.), it was confirmed that the carboxylic acid moiety is transformed to the glycerol ester. Structural formula of the reaction product thus obtained is shown below.

Figure 1:
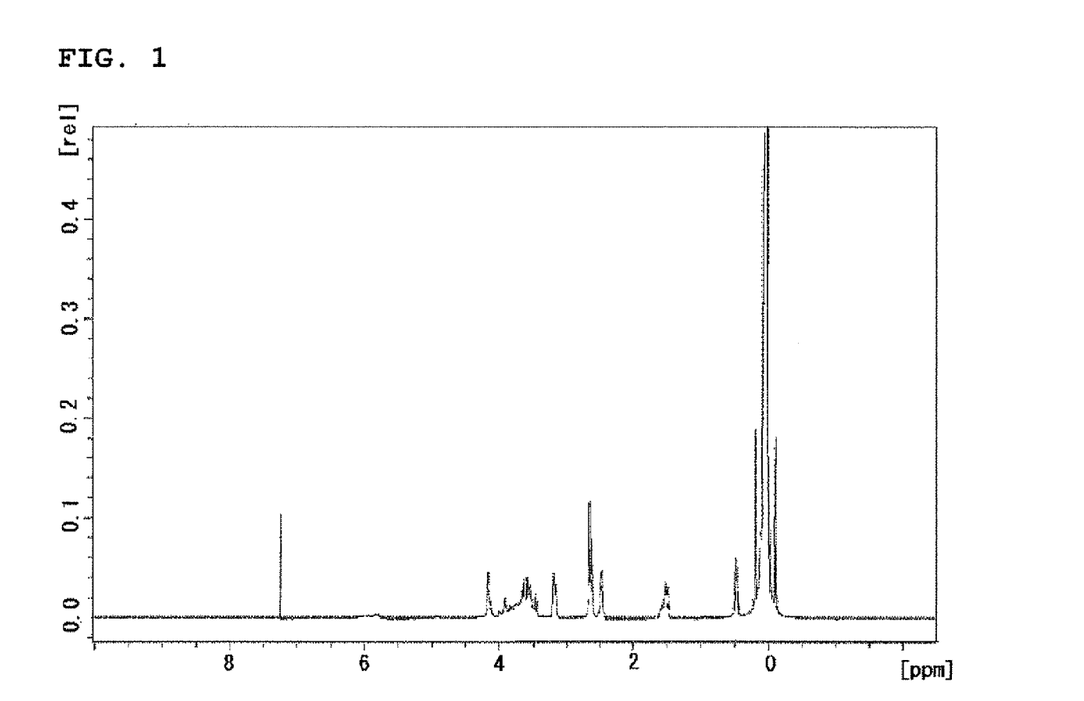
FIG. 1 is shows 1H NMR measurement result of the reaction product obtained in Preparation Example 1.

(R$^a$ = —CH$_2$-CH$_2$— and m' = 1)

Preparation Example 2

Into a reactor were taken 200 parts by mass of an amino-modified organopolysiloxane shown by the following average composition formula with viscosity of 57 mm$^2$/second (25° C.) and amine equivalent of 1230 g/mol, 20 parts by mass of tetrahydrofuran, and 16 parts by mass of succinic anhydride; and then, the resulting mixture was stirred at 50° C. for 3 hours. The reaction mixture thus obtained was stripped to remove the solvent under reduced pressure at 110° C. to obtain a colorless, transparent liquid having viscosity of 7600 mPa·s (25° C.). The carboxy equivalent of this liquid was 1340 g/mol, so that it was confirmed that conversion to the amidecarboxylic acid took place.

Then, 120 parts by mass of the liquid thus obtained, 13 parts by mass of glycidol, and 30 parts by mass of acetonitrile were stirred in a different reactor at 65° C. for 6 hours. The reaction mixture thus obtained was stripped to remove the solvent and the unreacted substance under reduced pressure at 120° C. to obtain a pale yellow, transparent liquid having viscosity of 16800 mPa·s (25° C.). Meanwhile, special purification processes such as washing, a hydrogenation reaction, neutralization, and removal of a neutralized salt were not carried out. From the measurement result (FIG. 2) of 1H NMR (CDC13, 400 MHz, manufactured by Bruker Corp.), it was confirmed that the carboxylic acid moiety is transformed to the glycerol ester. Structural formula of the reaction product thus obtained is shown below.

Figure 2:
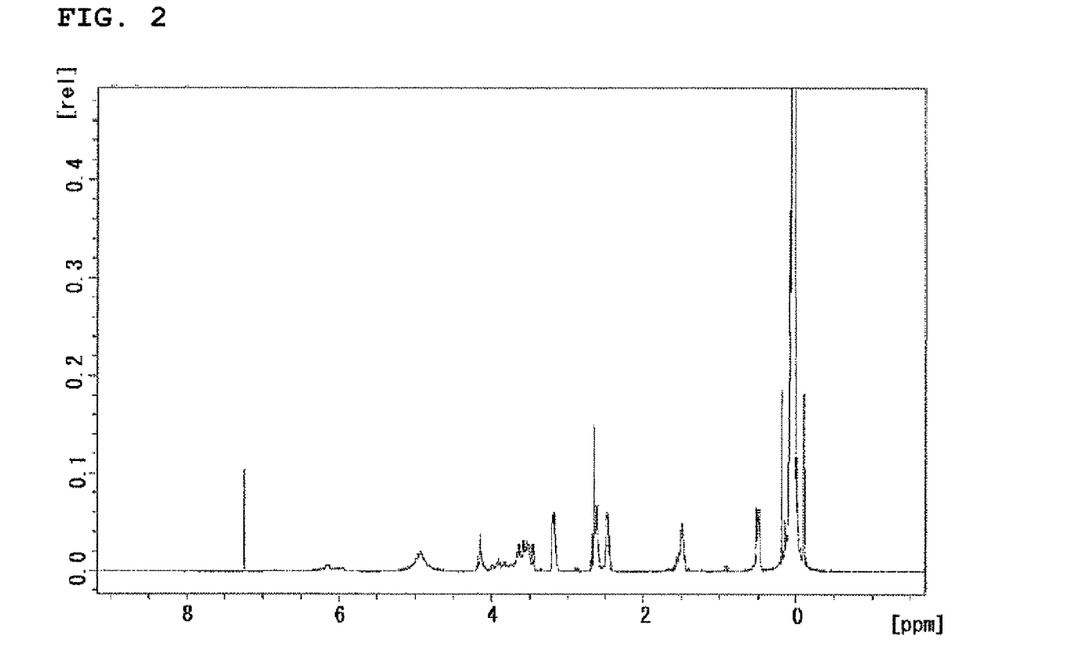
FIG. 2 is shows 1H NMR measurement result of the reaction product obtained in Preparation Example 2.

(R$^a$ = —CH$_2$-CH$_2$— and m' = 1)

Preparation Example 3

Into a reactor were taken 150 parts by mass of an amino-modified organopolysiloxane shown by the following average composition formula with viscosity of 110 mm$^2$/second (25° C.) and amine equivalent of 5090 g/mol, 20 parts by mass of tetrahydrofuran, and 3 parts by mass of succinic anhydride; and then, the resulting mixture was stirred at 50° C. for 3 hours. The reaction mixture thus obtained was stripped to remove the solvent under reduced pressure at 110° C. to obtain a colorless, transparent liquid having viscosity of 1260 mPa·s (25° C.). The carboxy equivalent of this liquid was 5240 g/mol, so that it was confirmed that conversion to the amidecarboxylic acid took place.

Then, 120 parts by mass of the liquid thus obtained, 9 parts by mass of glycidol, 0.2 parts by mass of triethylamine, and 30 parts by mass of tetrahydrofurane were stirred in a different reactor at 80° C. for 6 hours. The reaction mixture thus obtained was stripped to remove the solvent and the unreacted substance under reduced pressure at 120° C. to obtain a pale yellow, transparent liquid having viscosity of 134000 mPa·s (25° C.). Meanwhile, special purification processes such as washing, a hydrogenation reaction, neutralization, and removal of a neutralized salt were not carried out. From the measurement result of 1H NMR (CDC13, 400 MHz, manufactured by Bruker Corp.), characteristic peaks can be seen near 3.4 to 4.3 ppm, and it was confirmed that the carboxylic acid moiety is transformed to the glycerol ester. Structural formula of the reaction product thus obtained is shown below.

($R^a =$ —$CH_2$—$CH_2$— and $m' = 3$)

Preparation Example 4

Into a reactor were taken 150 parts by mass of an amino-modified organopolysiloxane shown by the following average composition formula with viscosity of 120 mm²/second (25° C.) and amine equivalent of 7450 g/mol, 20 parts by mass of tetrahydrofuran, and 2 parts by mass of maleic anhydride; and then, the resulting mixture was stirred at 50° C. for 3 hours. The reaction mixture thus obtained was stripped to remove the solvent under reduced pressure at 110° C. to obtain a colorless, transparent liquid having viscosity of 550 mm²/second (25° C.). The carboxy equivalent of this liquid was 7550 g/mol, so that it was confirmed that conversion to the amidecarboxylic acid took place.

Then, 130 parts by mass of the liquid thus obtained, 2.5 parts by mass of glycidol, and 40 parts by mass of 1,4-dioxane were stirred in a different reactor at 80° C. for 6 hours. The reaction mixture thus obtained was stripped to remove the solvent and the unreacted substance under reduced pressure at 120° C. to obtain a pale yellow, transparent liquid having viscosity of 2900 mm²/second (25° C.). Meanwhile, special purification processes such as washing, a hydrogenation reaction, neutralization, and removal of a neutralized salt were not carried out. From the measurement result of 1H NMR (CDC13, 400 MHz, manufactured by Bruker Corp.), characteristic peaks can be seen near 3.4 to 4.3 ppm, and it was confirmed that the carboxylic acid moiety is transformed to the glycerol ester. Structural formula of the reaction product thus obtained is shown below.

Preparation Example 5

Into a reactor were taken 400 parts by mass of an amino-modified organopolysiloxane shown by the following average composition formula with viscosity of 282 mm²/second (25° C.) and amine equivalent of 4890 g/mol, 50 parts by mass of tetrahydrofuran, and 8.2 parts by mass of succinic anhydride; and then, the resulting mixture was stirred at 50° C. for 3 hours. The reaction mixture thus obtained was stripped to remove the solvent under reduced pressure at 110° C. to obtain a colorless, transparent liquid having viscosity of 9200 mPa·s (25° C.). The carboxy equivalent of this liquid was 5040 g/mol, so that it was confirmed that conversion to the amidecarboxylic acid took place.

Then, 200 parts by mass of the liquid thus obtained, 8.8 parts by mass of glycidol, and 50 parts by mass of 2-propanol were stirred in a different reactor at 80° C. for 12 hours. The reaction mixture thus obtained was stripped to remove the solvent and the unreacted substance under reduced pressure at 120° C. to obtain a pale yellow, transparent liquid having viscosity of 15620 mPa·s (25° C.). Meanwhile, special purification processes such as washing, a hydrogenation reaction, neutralization, and removal of a neutralized salt were not carried out. From the measurement result of 1H NMR (CDC13, 400 MHz, manufactured by Bruker Corp.), characteristic peaks can be seen near 3.4 to 4.3 ppm, and it was confirmed that the carboxylic acid moiety is transformed to the glycerol ester. Structural formula of the reaction product thus obtained is shown below.

($R^a =$ —CH═CH— and $m' = 1$)

($R^a = $ —$CH_2$—$CH_2$— and $m' = 1$)

Preparation Example 6

Into a reactor were taken 200 parts by mass of an amino-modified organopolysiloxane shown by the following average composition formula with viscosity of 125 Pa·s (25° C.) and amine equivalent of 10000 g/mol, 50 parts by mass of tetrahydrofuran, and 3 parts by mass of phthalic anhydride; and then, the resulting mixture was stirred at 50° C. for 4 hours. The reaction mixture thus obtained was stripped to remove the solvent under reduced pressure at 110° C. to obtain a pale yellow, transparent gum-like liquid having viscosity of 1560 Pa·s (25° C.). The carboxy equivalent of this liquid was 10150 g/mol, so that it was confirmed that conversion to the amidecarboxylic acid took place.

Then, 150 parts by mass of the liquid thus obtained, 3 parts by mass of glycidol, and 40 parts by mass of tetrahydrofuran were stirred in a different reactor at 65° C. for 12 hours. The reaction mixture thus obtained was stripped to remove the solvent and the unreacted substance under reduced pressure at 120° C. to obtain a pale yellow, transparent liquid having viscosity of 1920 Pa·s (25° C.). Meanwhile, special purification processes such as washing, a hydrogenation reaction, neutralization, and removal of a neutralized salt were not carried out. From the measurement result of 1H NMR (CDC13, 400 MHz, manufactured by Bruker Corp.), characteristic peaks can be seen near 3.4 to 4.3 ppm, and it was confirmed that the carboxylic acid moiety is transformed to the glycerol ester. Structural formula of the reaction product thus obtained is shown below.

($R^a = $ phenylene group and $m' = 1$)

Comparative Preparation Example 1

Into a reactor were taken 300 parts by mass of a methylhydrogen organopolysiloxane shown by the following average composition formula with viscosity of 35 mm$^2$/second (25° C.),

100 parts by mass of 2-propanol, 45 parts by mass of allyl glycerol shown by the following average composition formula,

0.02 parts by mass of 1-butanol solution of chloroplatinic acid divinyl tetramethyl disiloxane complex (3% by mass of platinum), and 0.04 parts by mass of 10% ethanol solution of potassium acetate; and then, the resulting mixture was stirred at 80° C. for 5 hours. The reaction mixture thus obtained was stripped to remove the solvent under reduced pressure at 110° C. for 3 hours to obtain a colorless, slightly turbid liquid having viscosity of 4500 mm$^2$/second (25° C.).

Comparative Preparation Example 2

Into a reactor were taken 400 parts by mass of a methylhydrogen organopolysiloxane shown by the following average composition formula with viscosity of 78 mm$^2$/second (25° C.), 120 parts by mass of 2-propanol, 29 parts by mass of allyl glycerol shown by the following average composition formula, 0.02 parts by mass of 1-butanol solution of chloroplatinic acid divinyl tetramethyl disiloxane complex (3% by mass of platinum), and 0.04 parts by mass of 10% ethanol solution of potassium acetate; and then, the resulting mixture was stirred at 80° C. for 5 hours. The reaction mixture thus obtained was stripped to remove the solvent under reduced pressure at 110° C. for 3 hours to obtain a colorless, slightly turbid liquid having viscosity of 3120 mm²/second (25° C.).

Examples 1 to 3 and Comparative Examples 1 to 4

By a usual method, creams of the present invention and for comparison having compositions (% by mass) shown in Table 1 were prepared by using the reaction products obtained by the Preparation Examples 1 to 3 and Comparative Preparation Examples 1, 2 (Examples 1 to 3 and Comparative Examples 1 to 4).

Sensory evaluation of the obtained creams was carried out by the method shown below. The results are shown in Table 1.

<Method of Sensory Evaluation>

A cream shown in Table 1 with the amount thereof being 2 g was applied on a skin; and after fully familiarized with a skin, evaluation was carried out. Sensory evaluation was performed as to absence of stickiness, a moist feeling, durability of the moist feeling, odorlessness at the time of one month after preparation of the cream, and cream stability at the time of one month after preparation of the cream (stability in the Table). Evaluation criteria are as shown below based on number of the panelists (5 panelists) who replied with the answer, "Yes, effective".

Evaluation Criteria:
Excellent: 4 to 5 panelists with Yes
Good: 3 panelists with Yes
Fair; 2 panelists with Yes
Poor; 1 or zero panelist with Yes

TABLE 1

| | | Example | | | Comparative Example | | | |
|---|---|---|---|---|---|---|---|---|
| | | 1 | 2 | 3 | 1 | 2 | 3 | 4 |
| 1 | Glycerol group-containing-organopolysiloxane (Preparation Example 1) | 2 | | | | | | |
| 2 | Glycerol group-containing-organopolysiloxane (Preparation Example 2) | | 2 | | | | | |
| 3 | Glycerol group-containing-organopolysiloxane (Preparation Example 3) | | | 2 | | | | |
| 4 | Glycerol group-containing-organopolysiloxane (Comparative-Preparation Example 1) | | | | 2 | | | |
| 5 | Glycerol group-containing-organopolysiloxane (Comparative-Preparation Example 2) | | | | | 2 | | |
| 6 | Sofcare GS-G *1 | | | | | | 2 | |
| 7 | KF-6017 *2 | | | | | | | 2 |
| 8 | Dimethyl polysiloxane (6 mm²/second) | 6 | 6 | 6 | 6 | 6 | 6 | 6 |
| 9 | Squalane | 2 | 2 | 2 | 2 | 2 | 2 | 2 |
| 10 | Mineral oil | 1 | 1 | 1 | 1 | 1 | 1 | 1 |
| 11 | KSG-15 *3 | 8 | 8 | 8 | 8 | 8 | 8 | 8 |
| 12 | KSG-210 *4 | 1 | 1 | 1 | 1 | 1 | 1 | 1 |
| 13 | 1,3-Butylene glycol | 7 | 7 | 7 | 7 | 7 | 7 | 7 |
| 14 | Sodium citrate | 0.2 | 0.2 | 0.2 | 0.2 | 0.2 | 0.2 | 0.2 |
| 15 | Sodium chloride | 0.2 | 0.2 | 0.2 | 0.2 | 0.2 | 0.2 | 0.2 |
| 16 | Ethanol | 4 | 4 | 4 | 4 | 4 | 4 | 4 |

TABLE 1-continued

|   | | Example | | | Comparative Example | | | |
|---|---|---|---|---|---|---|---|---|
|   | | 1 | 2 | 3 | 1 | 2 | 3 | 4 |
| 17 | Purified water | Remainder | Remainder | Remainder | Remainder | Remainder | Remainder | Remainder |
| Evaluation | Absence of stickiness | Excellent | Excellent | Excellent | Good | Fair | Fair | Poor |
|   | Moist feeling | Excellent | Good | Excellent | Good | Good | Fair | Poor |
|   | Durability of moist feeling | Good | Excellent | Excellent | Fair | Fair | Poor | Fair |
|   | Odorlessness | Excellent | Excellent | Excellent | Poor | Poor | Good | Fair |
|   | Stability | Good | Good | Excellent | Fair | Good | Fair | Good |

*1 Sofcare GS-G: Branched glycerol-modified silicone (manufactured by Kao Corp.)
*2 KF-6017: Polyether-modified silicone (manufactured by Shin-Etsu Chemical Co., Ltd.)
*3 KSG-15: Dimethyl polysiloxane elastomer (manufactured by Shin-Etsu Chemical Co., Ltd.)
*4 KSG-210: Polyether-modified dimethyl polysiloxane elastomer (manufactured by Shin-Etsu Chemical Co., Ltd.)

From the results shown in Table 1, it can be seen that the creams of Examples 1 to 3 are creams not generating odor with passage of time while having a durable moist feeling without stickiness, as compared with the creams of Comparative Examples 1 to 4.

A hair treatment as shown below was prepared by a usual method.

Example 4

| Composition | % by mass |
|---|---|
| Octadecyloxy(2-hydroxypropyl)dimethylamine | 0.5 |
| Stearic acid dimethylaminopropylamide | 2.0 |
| Stearyl alcohol | 5.0 |
| Dipropylene glycol | 1.0 |
| Benzyl alcohol | 0.5 |
| Phenoxy ethanol | 0.1 |
| Organopolysiloxane obtained by Preparation Example 6 | 2.5 |
| Highly polymerized dimethyl polysiloxane*5 | 0.5 |
| Glycerin | 5.0 |
| Polypropylene glycol | 2.5 |
| Lanolin fatty acid | 0.5 |
| Sunflower oil | 0.5 |
| Lactic acid | 1.5 |
| Fragrance | 0.4 |
| Sodium hydroxide | appropriate amount |
| Deionized water | remainder |
| Total | 100.0 |

*5 KF-96H (100000 cs, manufactured by Shin-Etsu Chemical Co., Ltd.)

The hair treatment thus obtained did not change with passage of time, while having a moist feeling, smoothness, softness, and easy combing without stickiness.

Example 5

A liquid milky foundation having the composition as shown below was prepared by a usual method.
(Ingredients)

| Composition | % by mass |
|---|---|
| 1. Dimethyl polysiloxane (6 mm$^2$/second) | 5.0 |
| 2. Squlane | 4.0 |
| 3. Neopentyl glycol dioctanoate | 3.0 |
| 4. Diglyceride myristate isostearate | 2.0 |
| 5. α-Monoisostearyl glyceryl ether | 1.0 |
| 6. Organopolysiloxane obtained by Preparation Example 1 | 1.0 |
| 7. Aluminum distearate salt | 0.2 |
| 8. Powder dispersion element*6 | 26.2 |
| 9. Magnesium sulfate | 0.7 |
| 10. Glycerin | 3.0 |
| 11. Preservative | appropriate amount |
| 12. Fragrance | appropriate amount |
| 13. Purified water | remainder |
| Total | 100.0% |

*6 Decamethyl cyclopentasiloxane dispersion element of aluminum hydroxide and titanium oxide covered with stearic acid: SPD-T5 (manufactured by Shin-Etsu Chemical Co., Ltd.)

It was confirmed that the liquid milky foundation thus obtained has a light and wide spreading property with a moist and fresh use feeling and without oiliness and stickiness, while having good cosmetic durability and stability with time and temperature.

Example 6

An eye liner having the composition as shown below was prepared by a usual method.
(Ingredients)

| Composition | % by mass |
|---|---|
| 1. Decamethyl cyclopentasiloxane | 22.0 |
| 2. Dimethyl polysiloxane (6 mm$^2$/second) | 5.0 |
| 3. Black iron oxide | 20.0 |
| 4. Vitamin E acetate | 0.2 |
| 5. Jojoba oil | 2.0 |
| 6. Bentonite | 3.0 |
| 7. Organopolysiloxane obtained by Preparation Example 4 | 2.0 |
| 8. Ethanol | 10.0 |
| 9. 1,3-butylene glycol | 10.0 |
| 10. Preservative | appropriate amount |
| 11. Fragrance | appropriate amount |
| 12. Purified water | remainder |
| Total | 100.0% |

It was confirmed that the eye liner thus obtained has a light spreading property and thus is easy to draw; and in addition, it has a clean and fresh use feeling without stickiness. There was no change by temperature or passage of time; and in addition, it is excellent not only in usability, stability, water-resistance, and antiperspirant property but also in cosmetic durability.

It must be noted here that the present invention is not limited to the embodiments as described above. The foregoing embodiments are mere examples; any form having substantially the same composition as the technical concept described in claims of the present invention and showing similar effects is included in the technical scope of the present invention.

What is claimed is:

1. A glycerol group-containing organopolysiloxane wherein a glycerol group-containing substituent shown by the following general formula (1) is bonded to at least one silicon atom of a main chain organopolysiloxane segment, wherein each X and Y independently represents a divalent hydrocarbon group having 1 to 10 carbon atoms; m represents an integer of 0 to 4; Z represents an organic group shown by the following general formula (2); wherein $R^a$ represents a divalent hydrocarbon group having 2 to 12 carbon atoms; and m' represents an integer of 1 to wherein formula (2) is the following

2. The glycerol group-containing organopolysiloxane according to claim 1, wherein the glycerol group-containing organopolysiloxane is a reaction product between glycidol and an organopolysiloxane having a substituent shown by the following general formula (3) bonded to at least one silicon atom of a main chain organopolysiloxane segment, wherein Z' represents an organic group shown by the following general formula (4)

3. The glycerol group-containing organopolysiloxane according to claim 1, wherein the glycerol group-containing organopolysiloxane is a compound shown by the following average composition formula (5), wherein each R independently represents a group selected from a hydrogen atom, a hydroxyl group, an alkoxy group having 1 to 3 carbon atoms, an alkyl group having 1 to 30 carbon atoms, a fluoroalkyl group having 1 to 30 carbon atoms, an aryl group having 6 to 30 carbon atoms, and an aralkyl group having 7 to 30 carbon atoms; $R^{10}$ represents a substituent shown by the general formula (1); $R^{11}$ represents a group selected from $R^{10}$ and R; A represents an organopolysiloxane segment shown by the following general formula (6), and Q represents an oxygen atom or a divalent hydrocarbon group having 1 to 3 carbon atoms; in the general formulae (5) and (6), each of a, b, and c independently represents an integer of 0 to 3; e represents an integer of 0 to 100; f represents an integer of 0 to 20000; g represents an integer of 0 or 1; h represents an integer of 0 or 1; i represents an integer of 0 to 100; and j represents an integer of 0 to 10000; however, when $R^{11}$ is $R^{10}$, $1 \leq a+b+c+e+g+i$; and when $R^{11}$ is R, $1 \leq a+b+c+e+l$, wherein formula (6) is the following 4. The glycerol group-containing organopolysiloxane according to claim 2, wherein the glycerol group-containing organopolysiloxane is a compound shown by the following average composition formula (5), wherein each R independently represents a group selected from a hydrogen atom, a hydroxyl group, an alkoxy group having 1 to 3 carbon atoms, an alkyl group having 1 to 30 carbon atoms, a fluoroalkyl group having 1 to 30 carbon atoms, an aryl group having 6 to 30 carbon atoms, and an aralkyl group having 7 to 30 carbon atoms; $R^{10}$ represents a substituent shown by the general formula (1); $R^{11}$ represents a group selected from $R^{10}$ and R; A represents an organopolysiloxane segment shown by the following general formula (6), and Q represents an oxygen atom or a divalent hydrocarbon group having 1 to 3 carbon atoms; in the general formulae (5) and (6), each of a, b, and c independently represents an integer of 0 to 3; e represents an integer of 0 to 100; f represents an integer of 0 to 20000; g represents an integer of 0 or 1; h represents an integer of 0 or 1; i represents an integer of 0 to 100; and j represents an integer of 0 to 10000; however, when $R^{11}$ is $R^{10}$, $1 \leq a+b+c+e+g+i$; and when $R^{11}$ is R, $1 \leq a+b+c+e+l$, wherein formula (6) is the following 5. A cosmetic wherein the glycerol group-containing organopolysiloxane according to claim 1 is contained therein.

6. A cosmetic wherein the glycerol group-containing organopolysiloxane according to claim 2 is contained therein.

7. A cosmetic wherein the glycerol group-containing organopolysiloxane according to claim 3 is contained therein.

8. A cosmetic wherein the glycerol group-containing organopolysiloxane according to claim 4 is contained therein.

9. A cosmetic wherein the glycerol group-containing organopolysiloxane according to claim 1 and a dimethyl polysiloxane having viscosity of 100 mm$^2$/second or less at 25° C. are contained therein.

10. A cosmetic wherein the glycerol group-containing organopolysiloxane according to claim 2 and a dimethyl polysiloxane having viscosity of 100 mm$^2$/second or less at 25° C. are contained therein.

11. A cosmetic wherein the glycerol group-containing organopolysiloxane according to claim 3 and a dimethyl polysiloxane having viscosity of 100 mm$^2$/second or less at 25° C. are contained therein.

12. A cosmetic wherein the glycerol group-containing organopolysiloxane according to claim 4 and a dimethyl polysiloxane having viscosity of 100 mm$^2$/second or less at 25° C. are contained therein.

13. A method for producing a glycerol group-containing organopolysiloxane wherein glycidol is reacted with an organopolysiloxane having a substituent shown by the following general formula (3) bonded to at least one silicon atom of a main chain organopolysiloxane segment, wherein each X and Y independently represents a divalent hydrocarbon group having 1 to 10 carbon atoms; m represents an integer of 0 to 4; Z' represents an organic group shown by the following general formula (4); wherein R$^a$ represents a divalent hydrocarbon group having 2 to 12 carbon atoms, wherein formula (4) is the following

* * * * *